(12) United States Patent
Koppe et al.

(10) Patent No.: US 12,097,369 B2
(45) Date of Patent: Sep. 24, 2024

(54) ORTHOPEDIC DEVICE

(71) Applicant: Ottobock SE & Co. KGaA, Duderstadt (DE)

(72) Inventors: Mario Koppe, Göttingen (DE); Heiko Glindemann, Göttingen (DE); Bernhard Graimann, Obernfeld (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 441 days.

(21) Appl. No.: 15/733,065

(22) PCT Filed: Oct. 16, 2018

(86) PCT No.: PCT/EP2018/078243
§ 371 (c)(1),
(2) Date: May 6, 2020

(87) PCT Pub. No.: WO2019/091716
PCT Pub. Date: May 16, 2019

(65) Prior Publication Data
US 2021/0370060 A1    Dec. 2, 2021

(30) Foreign Application Priority Data

Nov. 10, 2017    (DE) .................... 10 2017 126 463.9

(51) Int. Cl.
*A61N 1/36*    (2006.01)
*A61F 2/72*    (2006.01)
(Continued)

(52) U.S. Cl.
CPC ............ *A61N 1/36014* (2013.01); *A61F 2/72* (2013.01); *A61F 5/0102* (2013.01); *A61N 1/0452* (2013.01); *A61N 1/0484* (2013.01)

(58) Field of Classification Search
CPC .............. A61N 1/36014; A61N 1/0452; A61N 1/0484; A61F 2/72; A61F 2/80;
(Continued)

(56) References Cited

U.S. PATENT DOCUMENTS 4,243,051 A     1/1981  Wittemann
8,591,599 B1   11/2013  Kaliki et al.
(Continued)

FOREIGN PATENT DOCUMENTS

CN    101403721 A    4/2009
CN    101842049 B    9/2010
(Continued)

OTHER PUBLICATIONS

Yu X, Mahajan BK, Shou W, Pan H. Materials, Mechanics, and Patterning Techniques for Elastomer-Based Stretchable Conductors. Micromachines. 2017; 8(1):7. https://doi.org/10.3390/mi8010007 (Year: 2017).*

(Continued)

*Primary Examiner* — Gary Jackson
*Assistant Examiner* — Alexander M Eisenberg
(74) *Attorney, Agent, or Firm* — HOLLAND & HART LLP (57) ABSTRACT

An orthopedic device with a base body for applying to a body part of a wearer, and at least one electrode for transcutaneously transmitting electrical signals. The at least one electrode features an electrically conductive textile and an electrically conductive polymer, wherein the electrically conductive textile is partially penetrated by the electrically inductive polymer and arranged in such a way that it comes into contact with the body part when the base body is applied.

16 Claims, 9 Drawing Sheets

(51) Int. Cl.
*A61F 5/01* (2006.01)
*A61N 1/04* (2006.01)

(58) Field of Classification Search
CPC .. A61F 2/68; A61F 5/0102; A61F 5/01; A61F 2002/6827
See application file for complete search history.

(56) References Cited

U.S. PATENT DOCUMENTS

| | | | |
|---|---|---|---|
| 2004/0009731 A1* | 1/2004 | Rabinowicz | A61N 1/04 |
| | | | 2/456 |
| 2010/0082088 A1* | 4/2010 | Fassih | A61N 1/325 |
| | | | 607/149 |
| 2010/0262052 A1 | 10/2010 | Lunau et al. | |
| 2010/0318195 A1 | 12/2010 | Kettwig et al. | |
| 2013/0338472 A1* | 12/2013 | Macia Barber | A61B 5/02055 |
| | | | 174/255 |
| 2014/0209351 A1* | 7/2014 | Reinhardt | A61N 1/0492 |
| | | | 174/126.2 |
| 2015/0216682 A1* | 8/2015 | Achyuta | A61F 2/72 |
| | | | 607/118 |
| 2017/0273590 A1* | 9/2017 | Maesani | A61B 5/291 |
| 2017/0340226 A1* | 11/2017 | Takagahara | A61B 5/28 |
| 2019/0208629 A1* | 7/2019 | Cho | H05K 1/038 |
| 2019/0217078 A1* | 7/2019 | Yang | A61N 1/0484 |
| 2021/0205619 A1* | 7/2021 | Wong | A61N 1/0492 |

FOREIGN PATENT DOCUMENTS

| | | |
|---|---|---|
| CN | 103596620 A | 2/2014 |
| CN | 205433673 U | 8/2016 |
| CN | 106551693 A | 4/2017 |
| CN | 106725418 A | 5/2017 |
| DE | 10 2007 035 409 A1 | 1/2009 |
| DE | 10 2007 046 886 A1 | 4/2009 |
| DE | 10 2009 013 470 A1 | 10/2010 |
| DE | 10 2011 101 583 A1 | 11/2012 |
| DE | 10 2013 225 702 A1 | 6/2015 |
| EP | 0 467 966 B1 | 6/1996 |
| EP | 1 021 986 A2 | 7/2000 |
| WO | 2009/015627 A2 | 2/2009 |
| WO | 2014/090927 A1 | 6/2014 |

OTHER PUBLICATIONS

"International Search Report and Written Opinion of the International Searching Authority," issued in connection with Int'l Appl. No. PCT/CN2020/119908, dated Feb. 12, 2019 (19 pages).

Chinese Patent Office, "Office Action and Search Report", issued in connection with Chinese Patent Application No. 201880071181 dated Oct. 19, 2022 (14 pages) (8 pages of English Translation and 6 pages of Original Document).

* cited by examiner

ORTHOPEDIC DEVICE

CROSS REFERENCE TO RELATED APPLICATIONS

This application is a U.S. National Entry and claims priority to PCT International Patent Application No. PCT/EP2018/078243, filed 16 Oct. 2018, and entitled "ORTHOPEDIC DEVICE," which claims priority to Germany Patent Application No. 10-2017-126-463.9 filed 10 Nov. 2017, the entire disclosures of which are incorporated herein by this reference.

TECHNICAL FIELD

The invention relates to an orthopedic device with a base body for applying to a body part of the wearer, wherein the device comprises at least one electrode for the transcutaneous transmission of electrical signals. The invention also relates to an electrode for such an orthopedic device and a method for producing such an electrode.

BACKGROUND

Such electrodes are used in various applications. For example, they are used for muscle stimulation, for instance to develop muscles via functional electrical stimulation (FES) or transcutaneous electrical nerve stimulation (TENS).

Here, electrical signals are transmitted via the electrodes to the body of the wearer of the orthopedic device, so that muscles are stimulated to move. Alternatively, it is also possible to use such electrodes to pick up electrical signals from a muscle or the skin of the wearer and to conduct them for further processing. These signals can be consulted to provide information on the physical condition, state of movement or other parameters of the wearer; they may also serve to control, for instance, an orthosis or prosthesis. Preferably, bio-signals such as myoelectric signals or impedance signals are captured.

To render possible the transmission of the electrical signals from the electrode and the orthopedic device to the body of the patient, it is necessary for the actual contact between the electrode and the skin of the patient to occur via an ionically conductive medium. The conduction of electrical signals from the skin of the patient can also be achieved via metallic electrodes. For example, it is known from DE 10 2009 013 470 A1 to arrange a gel cushion containing an ionically conductive liquid gel on the side of the electrode that faces towards the skin. A liquid-tight carrier material is situated on the opposite side of the gel cushion in order to prevent any of the liquid gel from leaking on this side of the electrode. To ensure as an effective an electrical contact as possible between the electrode, especially the liquid gel in the gel cushion, and the skin of the wearer, a gel or moisture film must be formed on the skin of the patient. The disadvantage is that the electrodes equipped with a hydrogel or liquid gel are sticky and as such can only ensure a good grip on the skin of the wearer for a short period of time. Sponge electrodes, however, become damp and greasy due to the fact that the liquid can be easily pressed out of them.

A similar electrode is described in EP 1 021 986 A2. In this case, a gel body filled with an electrically conductive gel is also situated on the side of a carrier material that faces towards the skin. EP 0 467 966 B1 describes an electrical stimulation electrode which enables the electrical signals to be coupled directly into the skin of the patient via a conductive cloth.

In the case of metallic electrodes, silver textiles or silver-coated textiles are often used. These have an anti-bacterial effect and are sufficiently electrically conductive. However, it is disadvantageous that they may cause irritation to the skin, especially if worn for long periods of time, and can also be corroded, particularly by sweat secreted by the wearer. If worn over a longer period of time, the electrodes lose their electrical conductivity, so that in particular the quality of the signals picked up declines and at a certain point, said signals can no longer be used to control protheses.

DE 10 2011 101 583 A1 describes an electrode with a layer, preferably made of a non-woven fabric, that is partially introduced in an electronically conductive polymer layer, such that the non-woven fabric layer protrudes from the polymer layer on one side. The non-woven fabric layer is designed to retain a liquid at least also due to its capillary force, so that a conductive liquid can be easily retained without leaking any gel and bringing about any associated disadvantages. However, it is also a disadvantage here that the production of the electrode is relatively complex, resulting in relatively high production costs.

SUMMARY

The invention aims to further develop an orthopedic device in such a way that it is easy and cost-effective to produce and a contact between the electrode and the base material of a base body of the orthopedic device can be produced in an easy and reliable manner.

An orthopedic device is, for instance, a prosthesis socket or a prosthesis liner, for example for an arm or leg prosthesis, wherein further elements and components of the prosthesis can be arranged on the prosthesis socket or the prosthesis liner. For example, an orthopedic device is an orthosis for the upper or lower limb or a bandage. An orthopedic device may comprise a control device, especially with an electronic data processing device, in order to process bio-signals, for example, and/or to send stimulation signals to the body and the surface of the skin. The control device generally has a micro-processor. The control device can be coupled with at least one sensor, preferably with several sensors, which may form part of the orthopedic device. The sensor or sensors may be used to determine action states. Kinetic sensors, such as force or torque sensors, and/or kinematic sensors, such as acceleration, speed or position sensors, and/or environmental sensors, such as ultra-sound or radar, may be used.

The invention solves the problem by way of an orthopedic device with a base body for applying to a body part of the wearer, wherein the device comprises at least one electrode for transcutaneously transmitting electrical signals, wherein the at least one electrode features an electrically conductive textile and an electrically conductive polymer, wherein the electrically conductive textile is partially penetrated by the electrically inductive polymer and arranged in such a way that it comes into contact with the body part when the base body is applied.

The electrically conductive textile is partially penetrated by the electrically conductive polymer. This means that the conductive textile protrudes from the conductive polymer on one side. It is especially preferable if this prevents the electrically conductive polymer from coming into contact with the body when the base body of the orthopedic device is applied to the body part of the wearer. In this case, only the electrically conductive textile comes into contact with it. This ensures that electrical signals can be picked up from the body part of the wearer in an especially effective and stable manner. Due to the electrically conductive polymer that penetrates the electrically conductive textile, the individual fibers of the textile are held in position, thereby enabling artifacts in the signal caused by intertextile movements to be greatly reduced or completely eliminated. The highly effective contact between the conductive polymer and the conductive textile ensures that an electrical contact between the two materials occurs across a large surface area, which ensures a robust structure.

However, it is also possible that the electrically conductive polymer has penetrated the textile to such an extent that it comes into contact with the skin of the wearer in at least one area. Alternatively or additionally, the textile may be equipped with a hole or an opening, so that the polymer comes into contact with the skin of the wearer in the area of the hole or opening.

Electrodes made from an electrically conductive polymer known from the prior art are susceptible to artifacts and unwelcome disruptions in the measurement signal; this is likely to be due to the smooth hydrophobic surface of the electrode made of such a polymer. Due to the effective contact between the conductive textile and the conductive polymer, this disadvantage is also considerably minimised or completely eliminated.

In addition, unlike the prior art where a non-woven material is partially contained in and protrudes from the electrically conductive polymer, it is not necessary to use any gels or other liquids in order to establish an effective contact between the skin of the wearer and the electrode. Rather, this is automatically ensured by the electrically conductive textile and the electrically conductive polymer that partially penetrates it.

The conductive textile is preferably a silver textile or a silver-coated textile. Alongside the anti-bacterial effect of the silver, this embodiment has the advantage that the textile is hydrophobic and therefore automatically forms a conductive liquid layer, which leads to an effective electrical contact between the electrically conductive textile and the skin of the wearer.

Preferably, the electrically conductive polymer is a silicone, a polyurethane or a thermoplastic polymer, each of which has electrically conductive particles. This silicone is hydrophobic and thus strictly limits the liquid accumulated on the hydrophilic textile, so that a corrosion of the silver can be minimized. This increases the service life of the corresponding electrodes and therefore the service life of the orthopedic device; it also reduces the risk of skin irritations.

The electrically conductive particles in the electrically conductive polymer are preferably metal particles, especially silver particles, or carbon particles, preferably in the form of soot particles, graphite particles or carbon nanotubes.

In a preferred configuration of the orthopedic device, the base body is made of a base body material and the at least one electrode is connected to the base body material, particularly cast or moulded in said material, and/or incorporated into a textile. This is particularly pertinent if the orthopedic device is a prosthesis liner or other component, specifically made from a polymer, preferably a silicone. This ensures an effective mechanical contact between the base body material of the base body and the electrode, so that the production method can be designed to be more simple and thus more cost-effective; it also reduces the risk of electrodes becoming detached from the base body, which also increases the service life of the orthopedic device and reduces the risk of skin irritations caused by defective orthopedic devices.

It is preferable if a fixing element, preferably a positive-locking element, is arranged on a side of the polymer facing away from the textile, by means of which the electrode is or can be fixed to the base body. Preferably, the positive-locking element may be a button or a screw. In this case, it is an advantage if a correspondingly designed second positive-locking element is situated on the base body that interacts with the positive-locking element of the electrode. Specifically, when using detachable positive-locking elements such as a button, a snap connector or a screw thread, which is screwed into a corresponding counter-thread, electrodes can be easily replaced or removed for cleaning and/or maintenance.

The at least one electrode is preferably connected to an electric conductor, which comprises a core made of an electrically conductive polymer and an electrically insulating coating. Here, it has been proven beneficial for the electrically conductive polymer of the electrode to be the same as the electrically conductive polymer of the core. This renders it especially easy to ensure that an effective electrical contact between the electrode and the electric conductor can be achieved. The use of an electrically conductive polymer as the core of the electric conductor ensures that the conductor also has elastic and flexible properties that are preferably not inferior to the elasticity properties of the base body of the orthopedic device, especially a prosthesis liner. As a result, even extreme mechanical loads cannot have an adverse effect on the functionality, even over a long period of time.

The electrically conductive textile preferably connects the electrode to the material of the base body of the orthopedic device, for example the liner. Here, the textile may be the only connection between the electrode and the base body material or it may be one of several. The additional connection between the electrode and the base body material is especially advantageous if the base body material is an elastomer which can only be connected to the electrically conductive polymer with great difficulty or not at all. This ensures that a sufficient mechanical connection can still be achieved. The electronically conductive textile is preferably designed in such a way that it extends across the entire contact surface of the electrode that is to come into contact with the body part. However, this is not necessary. For certain embodiments, it is beneficial if the electrically conductive textile is designed to be annular, wherein this also—but not exclusively—refers to circular configurations. In the present case, the term annular should be understood to mean any configuration of the geometric form of the electrically conductive textile that features a hole. Preferably, the electrically conductive polymer is preferably brought into contact with the body part of the patient through said hole when the base body is applied. In this case, the annular electrically conductive textile also comes into contact with the body part; however, to a large extent it also serves to connect the electrode to the base body material.

The invention also solves the task by way of an electrode for an orthopedic device as described here. It also solves the problem by way of a method for producing such an electrode, wherein the electrically conductive polymer, being either partially or completely hardened, and the electronically conductive textile are placed on top of one another and pressed together using pressure until the polymer partially penetrates the textile, preferably halfway.

BRIEF DESCRIPTION OF THE DRAWINGS

In the following, an example of an embodiment of the present invention will be explained in more detail by way of the attached figures: They show FIG. 1—the top view and sectional representation of an electrode in a section of a base body of an orthopedic device, FIGS. 2-6—schematic representations of different orthopedic devices according to examples of an embodiment of the present invention, FIG. 7—schematic sectional representations through embedded electrodes, FIG. 8—schematic top views of electrodes and FIGS. 9 and 10—schematic sectional representations through electrodes.

DETAILED DESCRIPTION

Figure 1:
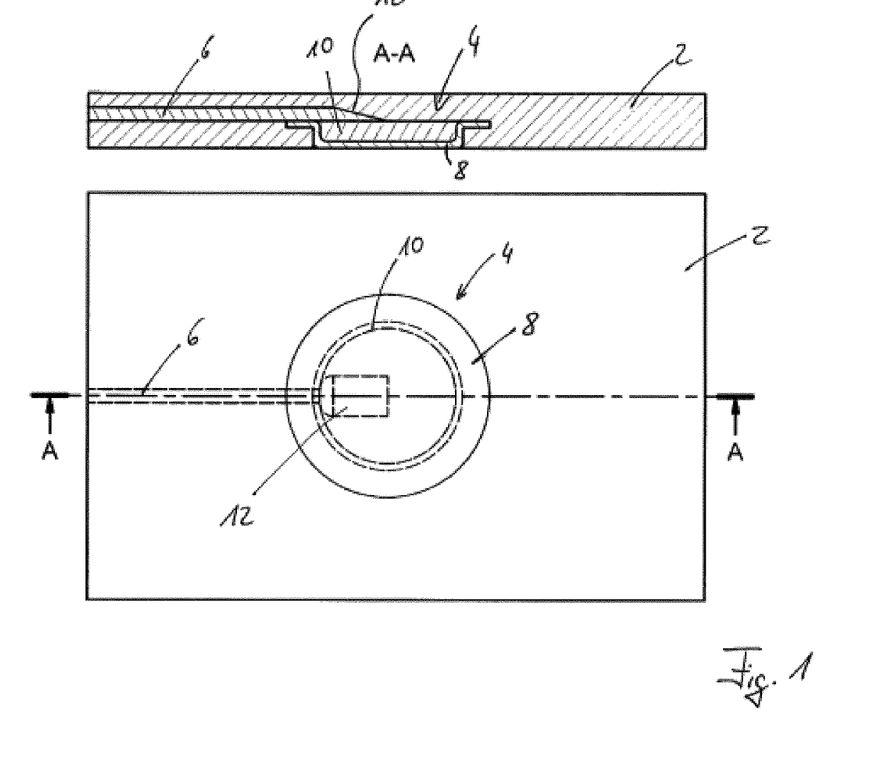

The lower part of FIG. 1 contains a top view of a section of a base body 2 of an orthopedic device according to a first example of an embodiment of the present invention. It is made of a silicone, for example, and comprises an electrode 4 that is connected to an electric conductor 6. FIG. 1 depicts a top view of a side that faces towards the body part of the wearer. The electrode 4 features a conductive textile 8, which comes into contact with the body of the wearer as soon as the base body 2 is arranged on the body part of the wearer. The conductive textile 8 is partially penetrated by a conductive polymer 10, so that an effective mechanical and electrical contact is established between the conductive textile 8 and the conductive polymer 10. The electric conductor 6 is connected to the electrode 4 in a contact region 12.

The upper part of FIG. 1 depicts a cross-section along the line A-A. The base body 2, in which the electric conductor 6 and the electrode 4 are situated, can be seen. The electrically conductive textile 8 is designed to be pot-shaped. The conductive polymer 10 is situated inside, wherein said polymer comes into contact with the electric conductor 6 in a contact region 12, in which the conductor 6 is bevelled. FIG. 1 does not show the partial penetration of the conductive textile by the conductive polymer.

Figure 2:
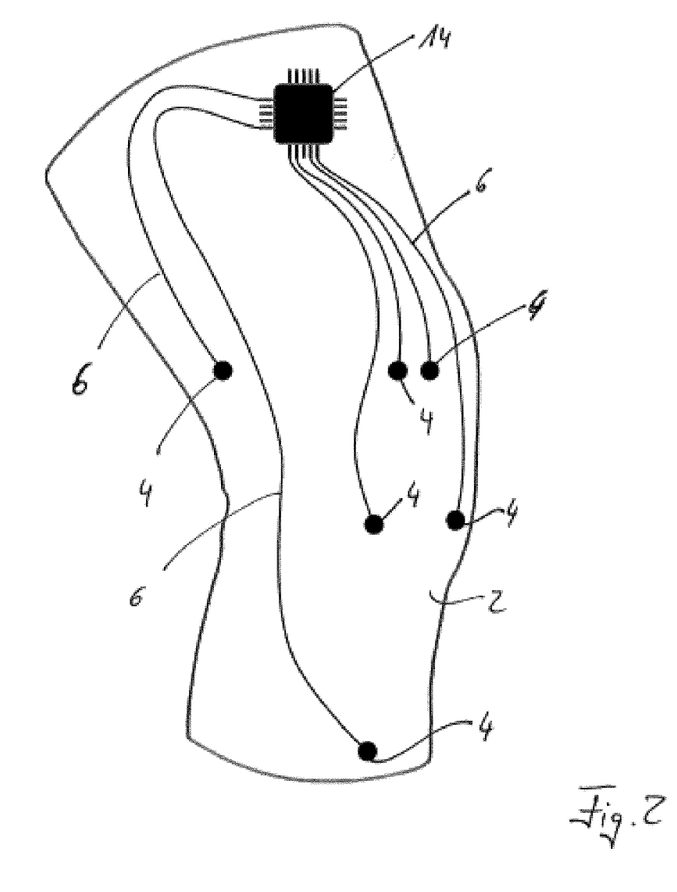

FIG. 2 depicts an orthopedic device in the form of a knee support. It has a base body 2, which can be made, for instance, of an elastic textile and may feature thickenings, pads or inserted or integrated padding elements. In the example of an embodiment shown, six electrodes 4 are integrated in the base body 2, each of which is connected to an electric conductor 6. The electric conductors 6 connect the electrodes 4 to an electric control system 14, which is depicted schematically in FIG. 2. The electric control system 14 is configured to further process electrical signals that are sent by the electrodes 4 via the electric conductor 6 to the electric control system 14 and, where applicable, to transfer them to an electronic data processing device. For example, this may occur via cables, not depicted in FIG. 2, which is especially advantageous if the electronic data processing device is arranged in the electric control system 14 or at least on the base body 2 of the orthopedic device. It may be practical, for instance, to further process the electrical signals transmitted by the electrodes 4 in the form of electronic data in the electric control system 14 in such a way that it can be stored in an electronic memory, which is preferably part of the orthopedic device, until it can be read and evaluated. Alternatively or additionally, it is beneficial to allow for a wireless transmission of the electronic data from the electric control system 14 to an electronic data processing device.

Figure 3:
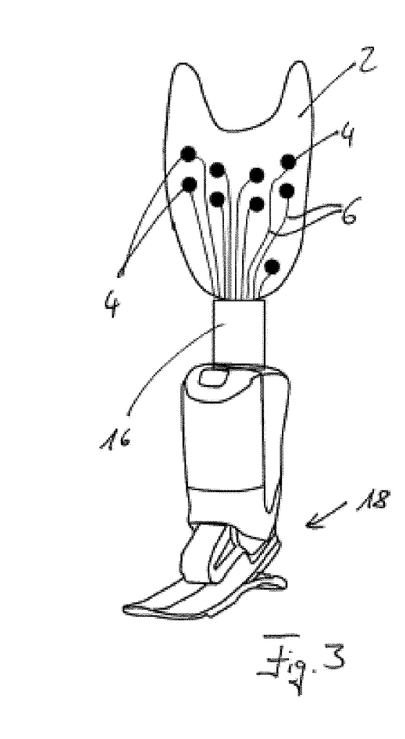

FIG. 3 shows an orthopedic device according to a further example of an embodiment of the present invention in the form of a lower leg prosthesis. The base body 2 is designed in the form of the prosthesis socket on which the electrodes 4 are arranged; these are connected to an electric control system via electric conductors 6, wherein said electric control system is not depicted. A lower leg element 16 and an artificial foot 18 are situated on the base body 2. Via the electrodes 6, myoelectric signals, for instance, can be picked up by an amputation stump that is arranged in the base body 2. These myoelectric signals are directed to the electric control system via the electric conductors 6 and used to control the artificial foot 18.

Figure 4:
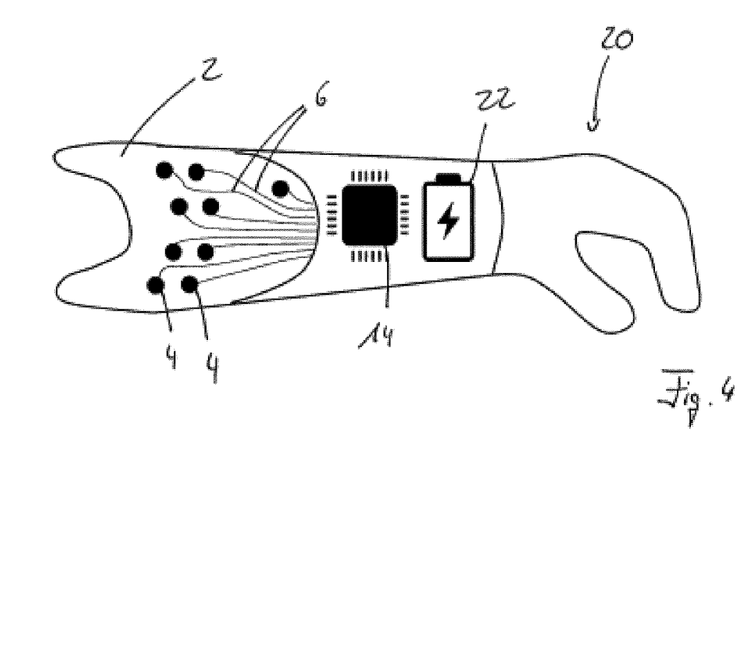

FIG. 4 depicts another embodiment of an orthopedic device according to an example of an embodiment of the present invention, which is also designed as a prosthesis; however, here it is designed as a hand or lower arm prosthesis. Here, the base body 2 also forms the prosthesis socket on which the electrodes 4 are arranged; these are connected to the electric control system 14 via electric conductors 6. The electric control system 14 is configured to generate control signals for a prosthetic hand 20 using the electrical signals picked up by the electrodes 4 and to thereby control the functions of the prosthetic hand 20. The orthopedic device shown in FIG. 4 also features a power supply 22 by means of which the electric control system 14 can be supplied with electrical energy.

Figure 5:
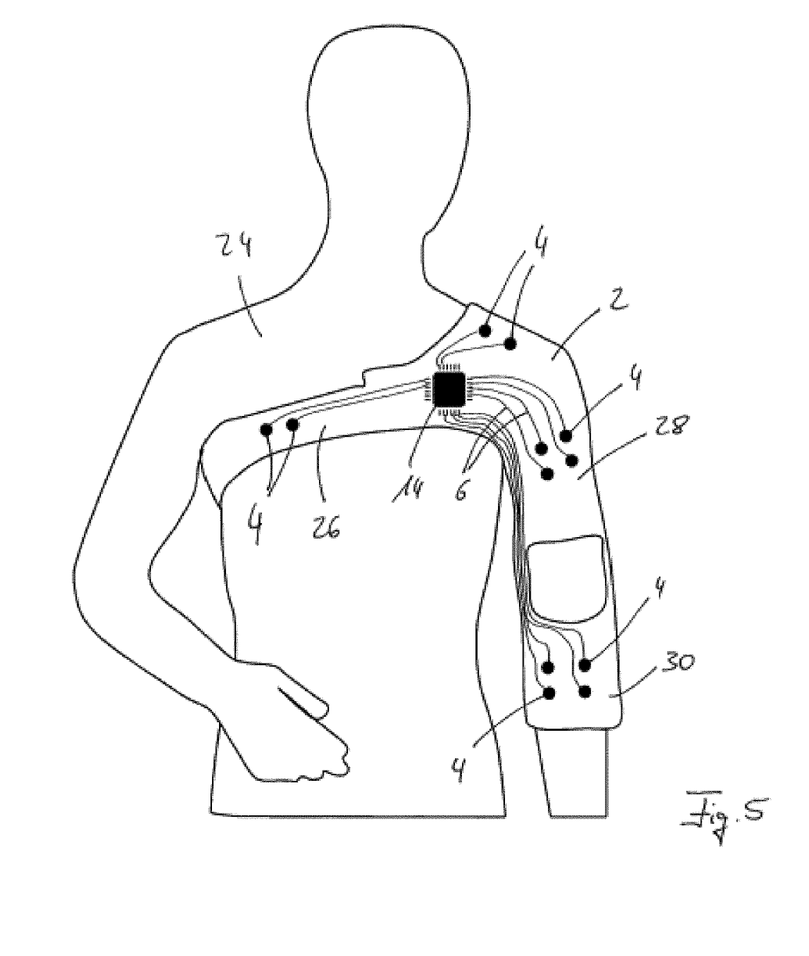

FIG. 5 depicts an embodiment of an orthopedic device which is designed as a shoulder orthosis. The base body 2 extends across the shoulder region of the wearer 24 and along the arm of the wearer 24 and over the elbow. The base body 2 has a fixing belt 26, which is guided around the torso of the wearer. Electrodes 4 are arranged on both the fixing belt 26, which forms part of the base body 2, and on other parts of the base body 2, such as an upper arm element 28 and a lower arm element 30; said electrodes are connected to the electric control system 14 via electric conductors 6.

FIG. 6 depicts an orthopedic device in the form of a t-shirt, wherein the base body 2 is the t-shirt itself. Electrodes 4 are arranged on both the sleeves 32 and the rest of the base body 2, wherein said electrodes are also connected to the electric control system 14 via electric conductors 6. The difficulty with this configuration of the orthopedic device is establishing as effective a contact as possible between the electrodes and the skin area of the wearer. This may be achieved, for instance, by way of the cut of the t-shirt, an elastic material or integrated belts.

Figure 7:
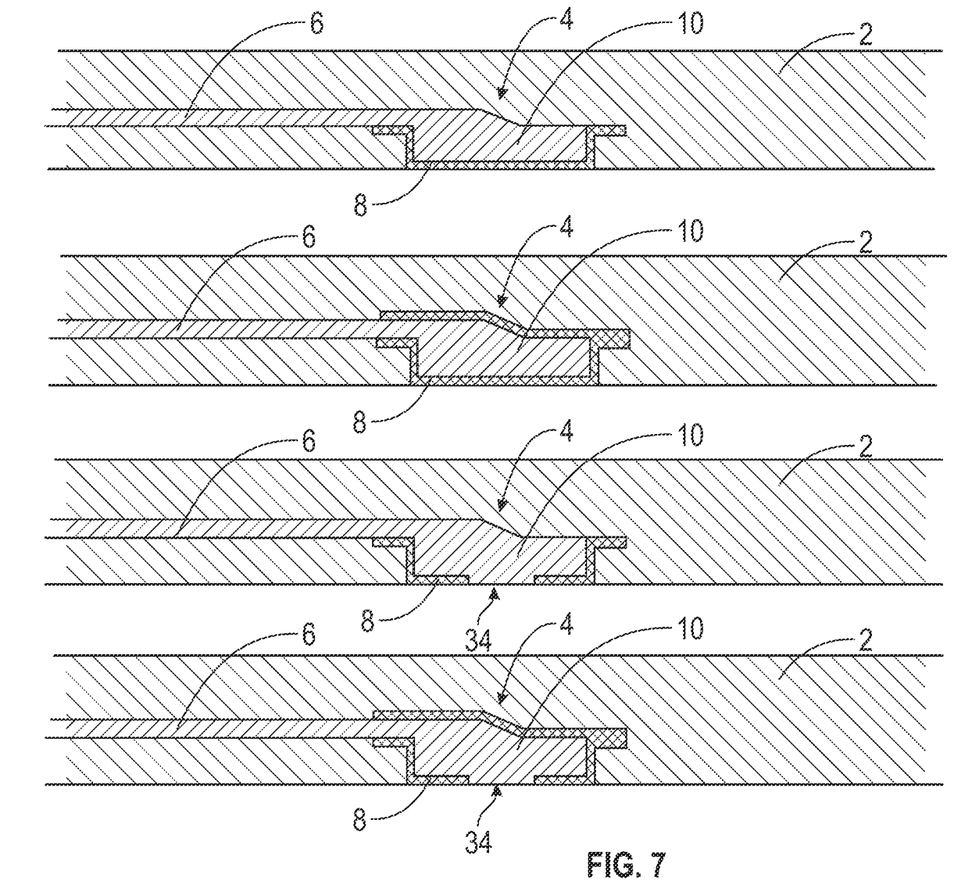

FIG. 7 shows four different sectional representations, each through an electrode 4 that is embedded in the base body 2 of an orthopedic device. It comprises a conductive polymer 10, which is connected to an electric conductor 6. The conductive textile 8, which in the two lower sectional representations comprises an opening 34, is situated on the underside of the respective base body 2 in FIG. 7, wherein said underside faces towards the body of the patient or wearer or the orthopedic device. At these points, the conductive polymer 10 comes into direct contact with the skin of the wearer. In the second and fourth representation from the top, the conductive textile 8 is not only situated on the specified underside, but also encloses the conductive polymer 10 on three sides. Specifically, it is also in the contact region between the base body 2 and the conductive polymer 10. At this point, the conductive textile 8 has the specific task of connecting the two polymers which can otherwise only be connected with great difficulty or not at all.

Figure 8:
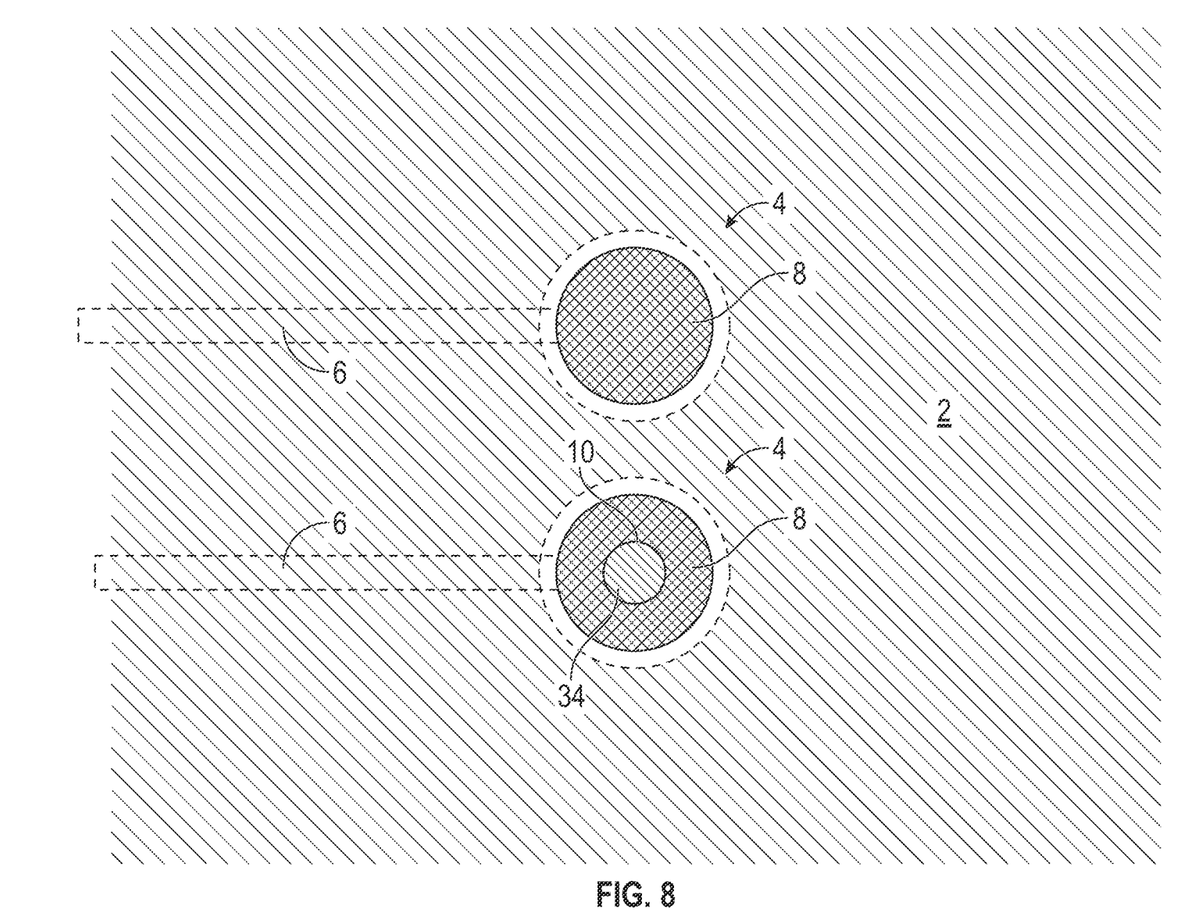

FIG. 8 contains two electrodes 4, which comprise differently designed conductive textiles 8. It depicts the schematic view from the side of the base body 2, which comes into contact with the skin of the wearer. The upper electrode 4 shown in FIG. 8 features a full-surface conductive textile 8, which comes into contact with the skin of the wearer. The lower representation shows an electrode 4, which features the previously described opening 34, by way of which the conductive polymer 10 comes into contact with the skin of the wearer. Both electrodes are connected via an electric conductor 6.

Figure 9:
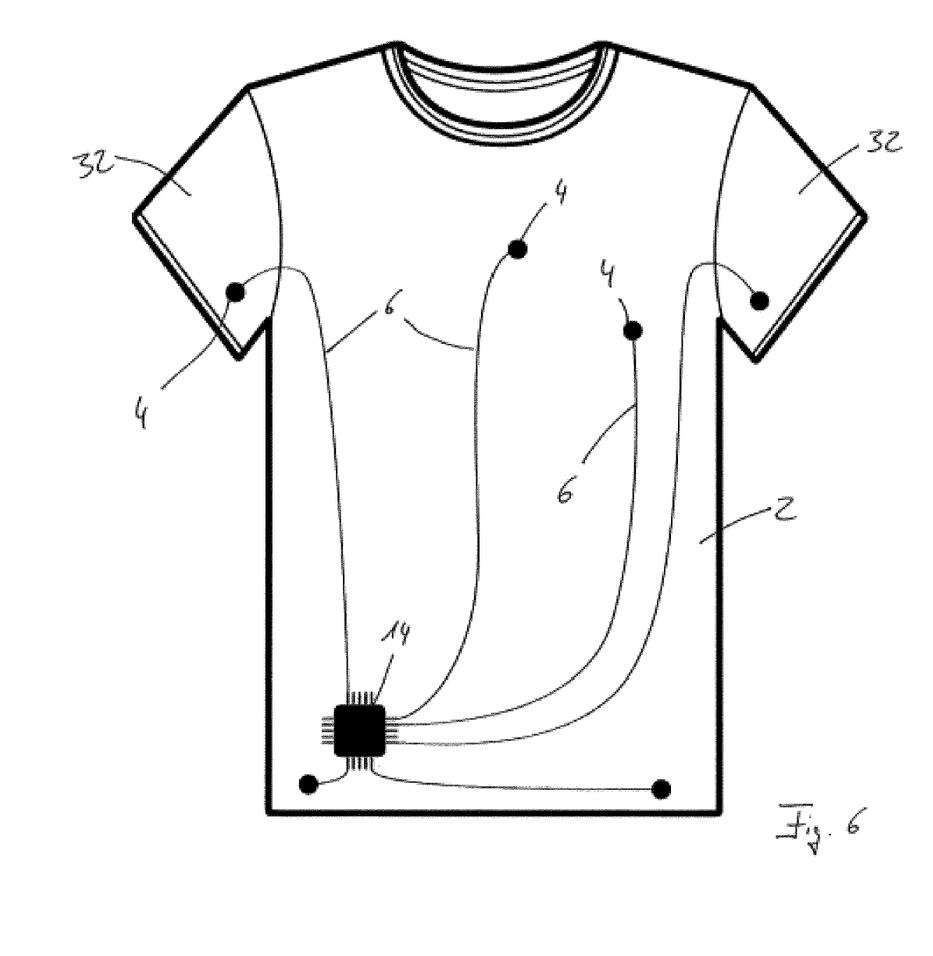

The upper part of FIG. 9 depicts the schematic sectional representation through the electrode 4, which corresponds to the uppermost representation in FIG. 7. The lower representation in FIG. 9 represents a more detailed view of the enclosed area. The material of the base body 2, the electrically conductive polymer 10 and the fiber structure of the conductive textile 8 can be clearly seen.

The sectional representation through the individual fibers 36 is shown. It is clear that the conductive polymer 10 has penetrated approximately halfway into the conductive textile 8. The individual fibers 36 feature microfibers 38, which ensure an effective contact and an effective connection to both the respective polymer of the base body 2 or the conductive polymer 10 and the skin of the wearer.

Figure 10:
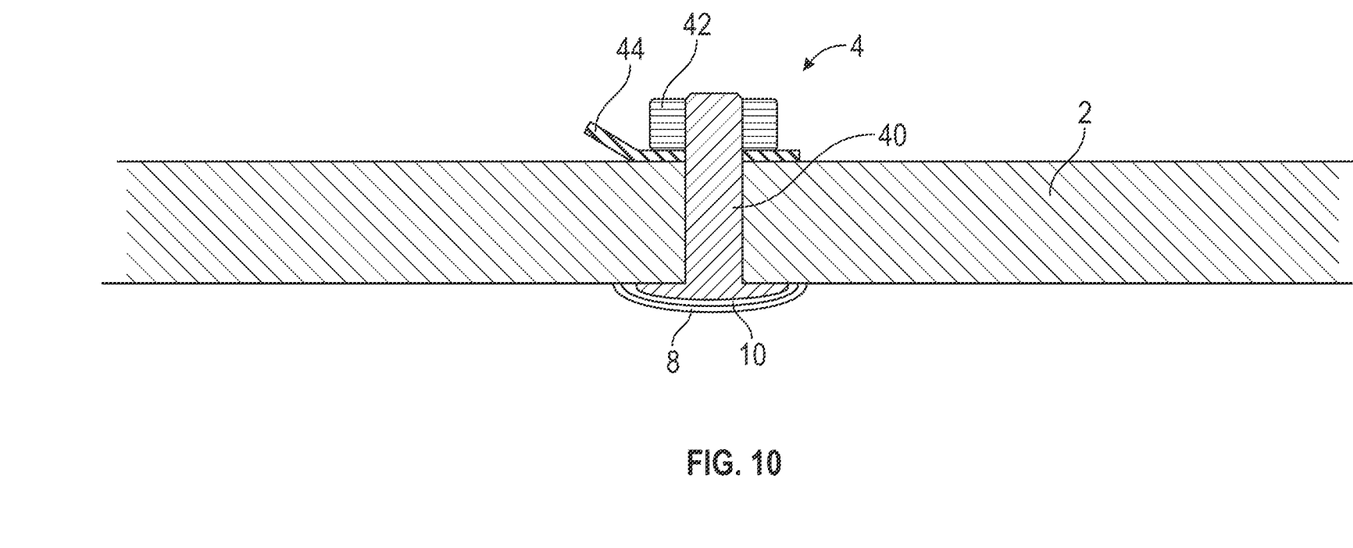

FIG. 10 shows a completely different configuration of the electrode 4. It comprises the conductive textile 8, which encloses a layer of conductive polymer 10 arranged on a screw 40. This is guided through the base body 2 of the orthopedic device and secured with a nut 42. Both the screw 40 and the nut 42 are preferably made of metal so as to establish an effective electrical contact. A cable lug 44 is arranged between the base body 2 and the nut 42, wherein said cable lug can be connected to the electric conductor 6.

We claim:

1. An orthopedic device comprising:
   a base body for applying to a body part of a wearer, the base body having a base body elasticity and a base body flexibility;
   at least one electrode for the transcutaneous transmission of electrical signals, the at least one electrode comprising:
   an electrically conductive textile;
   an electrically conductive polymer;
   wherein the electrically conductive textile is partially penetrated by the electrically conductive polymer and arranged in such a way that the electrically conductive textile comes into contact with the body part when the base body is applied, wherein the at least one electrode is connected to an electric conductor, wherein the electrical conductor comprises a core made of an electrically conductive polymer and an electrically insulating coating, the core having a core elasticity, and wherein the electrically conductive polymer of the electrode is the same as the electrically conductive polymer of the core.

2. The orthopedic device according to claim 1, wherein the conductive textile is a silver textile or a silver-coated textile.

3. The orthopedic device according to claim 1, wherein the electrically conductive polymer, of the at least one electrode and of the core is a silicone, a polyurethane, or a thermoplastic polymer, each including electrically conductive particles.

4. The orthopedic device according to claim 3, wherein the particles are metal particles or carbon particles.

5. The orthopedic device according to claim 1, wherein the base body comprises a base body material and the at least one electrode is connected to the base body material by at least one of casting or moulding the at least one electrode in the base body material, or incorporating the at least one electrode into a textile forming the base body material.

6. The orthopedic device according to claim 5, wherein a fixing element is arranged on a side of the electrically conductive polymer facing away from the textile, and the at least one electrode is or can be fixed to the base body by the fixing element.

7. An electrode for an orthopedic device according to claim 1.

8. A method for producing an electrode according to claim 7, wherein the electrically conductive polymer is either partially or completely hardened or partially or completely cross-linked, and the electronically conductive textile and electrically conductive polymer are placed on top of one another and pressed together using pressure until the electrically conductive polymer partially penetrates the electrically conductive textile.

9. An orthopedic device comprising:
   a base body configured to be applied to a body part of a wearer, the base body having a base body elasticity and a base body flexibility;
   at least one electrode to transcutaneously transmit electrical signals, the at least one electrode comprising:
   an electrically conductive polymer;
   an electrically conductive textile at least partially enclosing the electrically conductive polymer, wherein the electrically conductive textile defines an opening, the electrically conductive polymer extends through the opening, and the electrically conductive polymer is arranged to contact the body part when the base body is applied to the body part, wherein the at least one electrode is connected to an electric conductor, wherein the electrical conductor comprises a core made of an electrically conductive polymer and an electrically insulating coating, the core having a core elasticity, and wherein the electrically conductive polymer of the electrode is the same as the electrically conductive polymer of the core.

10. The orthopedic device according to claim 9, wherein the conductive textile comprises a silver textile or a silver-coated textile.

11. The orthopedic device according to claim 9, wherein the electrically conductive polymer of the at least one electrode and of the core comprises a silicone, a polyurethane, or a thermoplastic polymer, each including electrically conductive particles.

12. The orthopedic device according to claim 11, wherein the electrically conductive particles are metal particles or carbon particles.

13. The orthopedic device according to claim 9, wherein the base body is made of a base body material and the at least one electrode is connected to the base body material by casting or moulding in the base body material, or being incorporated into a textile forming the base body material.

14. The orthopedic device according to claim 13, wherein a fixing element is arranged on a side of the electrically conductive polymer facing away from the textile, and the electrode is or can be fixed to the base body by the fixing element.

15. The orthopedic device according to claim 14, wherein the fixing element includes a positive-locking element, which includes a button or a screw.

16. The orthopedic device according to claim 12, wherein the metal particles include silver, and the carbon particles include soot particles, graphite particles or carbon nanotubes.

\* \* \* \* \*